United States Patent [19]
Morioka et al.

[11] Patent Number: 5,274,434
[45] Date of Patent: Dec. 28, 1993

[54] METHOD AND APPARATUS FOR INSPECTING FOREIGN PARTICLES ON REAL TIME BASIS IN SEMICONDUCTOR MASS PRODUCTION LINE

[75] Inventors: Hiroshi Morioka, Ebina; Minori Noguchi, Yokohama; Yoshimasa Ohshima, Yokohama; Yukio Kembo, Yokohama; Yuzo Taniguchi, Higashimurayama, all of Japan

[73] Assignee: Hitachi, Ltd., Tokyo, Japan

[21] Appl. No.: 778,363

[22] Filed: Oct. 17, 1991

Related U.S. Application Data

[63] Continuation-in-part of Ser. No. 679,317, Apr. 2, 1991, Pat. No. 5,233,191.

[30] Foreign Application Priority Data

Oct. 17, 1990 [JP] Japan .................. 2-276253

[51] Int. Cl.⁵ ............... G01N 21/89; G02B 27/46; G06F 15/46
[52] U.S. Cl. ................... 356/237; 356/237; 437/8; 437/939
[58] Field of Search .......... 356/237; 437/8, 939

[56] References Cited

U.S. PATENT DOCUMENTS

| | | | |
|---|---|---|---|
| 3,658,420 | 4/1972 | Axelrod | 356/237 X |
| 4,376,583 | 3/1983 | Alford et al. | 356/237 |
| 4,378,159 | 3/1983 | Galbraith | 356/237 |
| 4,441,124 | 4/1984 | Heebner et al. | 356/237 X |
| 4,571,685 | 2/1986 | Kamoshida | 437/8 X |
| 4,614,427 | 9/1986 | Koizumi et al. | 356/237 |
| 4,806,774 | 2/1989 | Lin et al. | 356/237 X |

FOREIGN PATENT DOCUMENTS 59-65428 4/1984 Japan .

OTHER PUBLICATIONS

"Scanning Laser Senses Wafer Defects" Electronics Mar. 16, 1978, vol. 51 #6, pp. 48 and 50 copy 356/237.

*Primary Examiner*—Vincent P. McGraw
*Attorney, Agent, or Firm*—Antonelli, Terry Stout & Kraus

[57] ABSTRACT

In a mass production line of a semiconductor manufacturing process, foreign particle inspection method and apparatus for preventing occurrence of large quantities of defects and for keeping a necessary yield. The inspection apparatus is made up in a small-sized apparatus and disposed at inlet/outlet of processing apparatuses of the production line or to a transfer system between the processing apparatuses. The inspection apparatus includes at least one monitor for real-time sampling foreign particles possible deposited on wafer which is being carried by the transfer system, thereby enabling simplification in construction of the production line and reduction of manufacturing cost. The inspection apparatus may comprise a refractive index changeable type lens array, a spatial filter and a pattern data elimination circuit, and makes possible to conduct foreign particle inspection on repetitively-patterned portions of the wafers during transfer. With the spatial filter for eliminating repetitive data of the repetition patterns the small-sized compact inspection apparatus is capable of real-time inspecting the foreign particles on the wafers at a high speed.

20 Claims, 18 Drawing Sheets

METHOD AND APPARATUS FOR INSPECTING FOREIGN PARTICLES ON REAL TIME BASIS IN SEMICONDUCTOR MASS PRODUCTION LINE

CROSS-REFERENCE TO RELATED APPLICATION

This application is a continuation-in-part application of U.S. patent application Ser. No. 07/679,317, now U.S. Pat. No. 5,233,191 filed Apr. 2, 1991.

BACKGROUND OF THE INVENTION

This invention relates to a method and apparatus for inspecting any foreign matters or particles by a foreign particles monitor which conducts dust generation evaluation in a mass production line of a semiconductor fabrication process through product wafers.

If any foreign matters or particles exist on a wafer during a semiconductor fabrication process, they will result in defects such as defective insulation and short-circuit of wirings. When a semiconductor device is further miniaturized and if any foreign particles exist in a wafer, they will result in breakdown of a capacitor insulation film and a gate oxide film. These foreign particles are generated and mixed for various reasons and under various conditions. For example, some of them develop from driving portions of a transport unit and from the human body, while the other are produced as reaction products inside a processing apparatus due to a process gas, or are contained in chemicals and starting materials.

The conventional technique of this kind for detecting the foreign particles on the wafer irradiates a laser beam on the wafer, detects scattering light from the foreign particles generated when they adhere to the wafer, compares this detection result with the inspection result of the same kind of the wafer that is immediately before inspected so as to eliminate lie detection resulting from patterns and makes it possible to carry out high sensitivity and high reliability foreign particle inspection, as disclosed in JP-A-62-89336, for example.

Another prior art reference, JP-A-63-135848, discloses a technique which irradiates a laser beam on the wafer, detects scattering light from the foreign particles when they adhere to the wafer, and analyzes the detected foreign particle by analytical technique such as laser photoluminescence or XMR.

One of the main operations for start-up of mass production of LSIs is the operation for clarifying the causes of generation of these foreign particles and for considering an appropriate counter-measure, and detection of the generated foreign particles and analysis of the kinds of elements contained therein give a major key to the clarification of the cause. In a mass production line, on the other hand, the generation of these foreign particles must be detected as soon as possible and any counter-measure must be taken. If a long time passes away from the generation of the foreign particles to the detection of their generation, the number of defects becomes greater and a fabrication yield drops. Therefore, it is imperative to shorten the time from the occurrence of the foreign particle to its detection in order to keep a high fabrication yield. In other words, to maximize the effect of foreign particle inspection, a sampling time of a monitor must be reduced and ideally, real time sampling is preferably made for a mass production line.

However, the prior art references do not clearly distinguish between the state of mass production start-up and the state of a mass production line in a semiconductor fabrication process, and adapt those inspection apparatuses, which are used for the mass production start-up operations, as such to the mass production line. Although the generation of the foreign particles must be detected as soon as possible in the mass production line and appropriate counter-measures must be taken, the conventional inspection apparatuses are of a stand-alone type and inspect the foreign particles by bringing the wafers processed in the production line to the sites of the inspection apparatuses. This means that a long period of time is necessary for the transfer of the wafers and for the foreign particle inspection and hence, the inspection frequency cannot be raised to a sufficient value.

According to the above-mentioned techniques, the inspection apparatuses are great in scale and the foreign particle inspection requires a long time. In order to accomplish a real time monitor by using these conventional apparatuses, therefore, it is necessary to arrange a large number of large-scale apparatuses and this is practically unfeasible. In practice, one wafer has been sampled from one or several lots, or everyday, and this has been a practical limit. If the foreign particle inspection is carried out at such a frequency, the generation of the foreign particles cannot be detected sufficiently rapidly. In other words, the conventional sampling frequency is far apart from the ideal real time sampling. Still another problem with the prior art technique is that a necessary number of monitors must be disposed at sufficient positions in order to reduce the number of man-hours and equipments in the mass production line.

One of the principal operations for the mass production start-up of LSIs is an operation for clarifying the causes the generation of these foreign particles and for taking appropriate counter-measures and to this end, detection of the generated foreign particles and analysis of the kinds of elements will give a major key to the clarification of the causes of the generation of the foreign particles.

U.S. patent application Ser. No. 07/679,317 dated Apr. 2, 1991, entitled "METHOD AND APPARATUS OF INSPECTING FOREIGN MATTERS DURING MASS PRODUCTION START-UP AND MASS PRODUCTION LINE IN SEMICONDUCTOR PRODUCTION PROCESS", which relates to an improvement in the functions such as detection, analysis, evaluation, etc. in the start-up of mass-production operations, is assigned to the Assignee of the present application. The disclosure of the preceding application is herein incorporated by reference.

SUMMARY OF THE INVENTION

The present invention has principal objects of providing methods and apparatuses for foreign particles or particles real time inspection in mass production lines.

According to one aspect of the present invention, a foreign particle inspection apparatus is made compact in scale and is set to input/output ports of a processing apparatus of a semiconductor production line or it is set in a transfer system between processing apparatuses in order to accomplish real time sampling.

More definitely, the object described above can be accomplished by an apparatus for inspecting any foreign particles on a wafer during the fabrication of semiconductor devices, which comprises a stage on which the wafers are set, an illumination system for illuminating a measuring position on the wafer in a linear shape by a plane wave having a substantially single wavelength, a lens for imaging the illuminating position on a detector, a spatial filter so disposed as to cut off or block a diffraction light from repetition patterns on the wafers at an intermediate portion of the imaging optical system, a detector for detecting the imaged optical signal, a circuit for binarizing the signal detected by the detector, a circuit for taking out only the signal binarized isolatedly inside the wafer, and means for erasing the signal generated repeatedly between chips inside the wafers among the signals taken out.

During the mass production start-up of the semiconductor production process, individual process steps and equipments are evaluated by an expensive evaluation apparatus having high performance in order to evaluate and improve (debug) the material, process steps, equipments and designs and during the mass production, on the other hand, the number of process steps and equipments in the production line are reduced as much as possible and especially, the number of items of inspection and evaluation is reduced, in order to reduce the time necessary for the inspection and evaluation. To this end, causes of the generation of the foreign particles must be clarified by the use of a foreign particle detection/analysis system in which a sampling wafer is so contrived as to insure smooth and quick evaluation at the time of the mass production start-up, and the specification for inspection at the time of acceptance of delivered materials is changed or counter-measures are taken in the equipments for the foreign particle generation sources. These results are also fed back to the respective materials, processes, equipments, and the like, so as to change the process specification, which is otherwise likely to generate the foreign particles, to design a specification of devices which are highly resistant to the generation of the foreign particles, and at the same time, they are also utilized for the preparation of the specification for the inspection and evaluation of the mass production line. A foreign particle monitor is disposed on a product wafer, whenever necessary, at positions at which the foreign particles are likely to be generated, or a monitor is provided with the function of only monitoring the increase and decrease of specific foreign particle(s) at a specific position.

If the state of the mass production start-up and the state of the mass production line are divided from each other as described above, an apparatus or apparatuses for detecting, analyzing and evaluating the foreign particles at the time of the mass production start-up are allowed to operate efficiently. In this way, the mass production start-up can be made quickly, the foreign particle inspection/evaluation equipment used in the mass production line can be modified to a minimum necessary, simplified monitor apparatus, and simplification of the mass production line can be achieved.

In accordance with another aspect of the present invention, the following method is taken into specific consideration in order to accomplish a compact and high-speed inspection apparatus having equivalent functions to those of conventional large-scale inspection apparatus by means of the technologies available at process. First of all, repetitiveness is taken into specific consideration. A method of eliminating the repetition patterns and detecting defects is known conventionally, and this method can reliably secure detection performance.

A large number of technologies have been known in the past which discriminate and detect foreign particles and defects from a pattern by utilizing repetitiveness of a memory. However, it is not known that these technologies can be advantageously used for accomplishing a compact monitor for the monitor apparatus of the mass production line in accordance with the present invention described above. The monitor in this case need not at all monitor all the points on a given wafer, but may only monitor the points on the wafer at a certain specific ratio. In the fabrication of memories having a large number of repetition patterns, a great effect can be obtained if the monitor monitors only this repetition portion of the memories.

When coherent light is illuminated in the repetition patterns, light outgoes only in a certain specific direction. In other words, the light outgoing in the specific direction from the repetition portion in the case of the memories can be blocked by a spatial filter and hence, the foreign particles which do not occur repeatedly can be detected with high sensitivity. If a liquid crystal is used as the spatial filter in this case, the shape of the spatial filter can be changed arbitrarily through ON/OFF of the liquid crystals, so that arbitrary repetition patterns can be automatically inspected.

The means described above can improve the yield in the semiconductor production for the following reasons. It has been found afresh through strict detection experiments of the number of individual foreign particles on a wafer that the number of the individual foreign particles does not increase or decrease gradually but does quite sudden. It has been believed conventionally that the number of the individual foreign particles increases or decreases gradually and hence, the foreign particle inspection has been carried out at a sampling rate of one wafer a day from a lot, or once a day. At this sampling rate, however, the sudden increase of the foreign particles is overlooked, or the foreign particles are detected only after the number of them has increased to certain extents. Accordingly, a considerable number of defects occur unavoidably. The generation of the foreign particles must be detected as soon as possible and a counter-measure must be taken immediately, and if a certain period of time has passed away from the generation of the foreign particles till their detection, the number of the defects becomes greater and the yield becomes lower. A high production yield can be maintained by shortening the time passed from the generation of the foreign particles till their detection. This means that the sampling time of the monitor can be shortened and ideally, the effect of the foreign particle inspection can be exhibited to the maximum extent by effecting real time sampling.

Furthermore, the inspection in the conventional inspection apparatuses has been carried out by sampling a wafer and in this case, new foreign particles adhere onto the inspected wafer, and lowers the yield, as well. In contrast, in the foreign particle inspection apparatus of the present invention, the foreign particle inspection can be carried out without withdrawing a product wafer or wafers, so that the drop of the yield due to adhesion of the foreign particles to the withdrawn wafer(s) can be eliminated.

DESCRIPTION OF THE PREFERRED EMBODIMENTS

Figure 1:
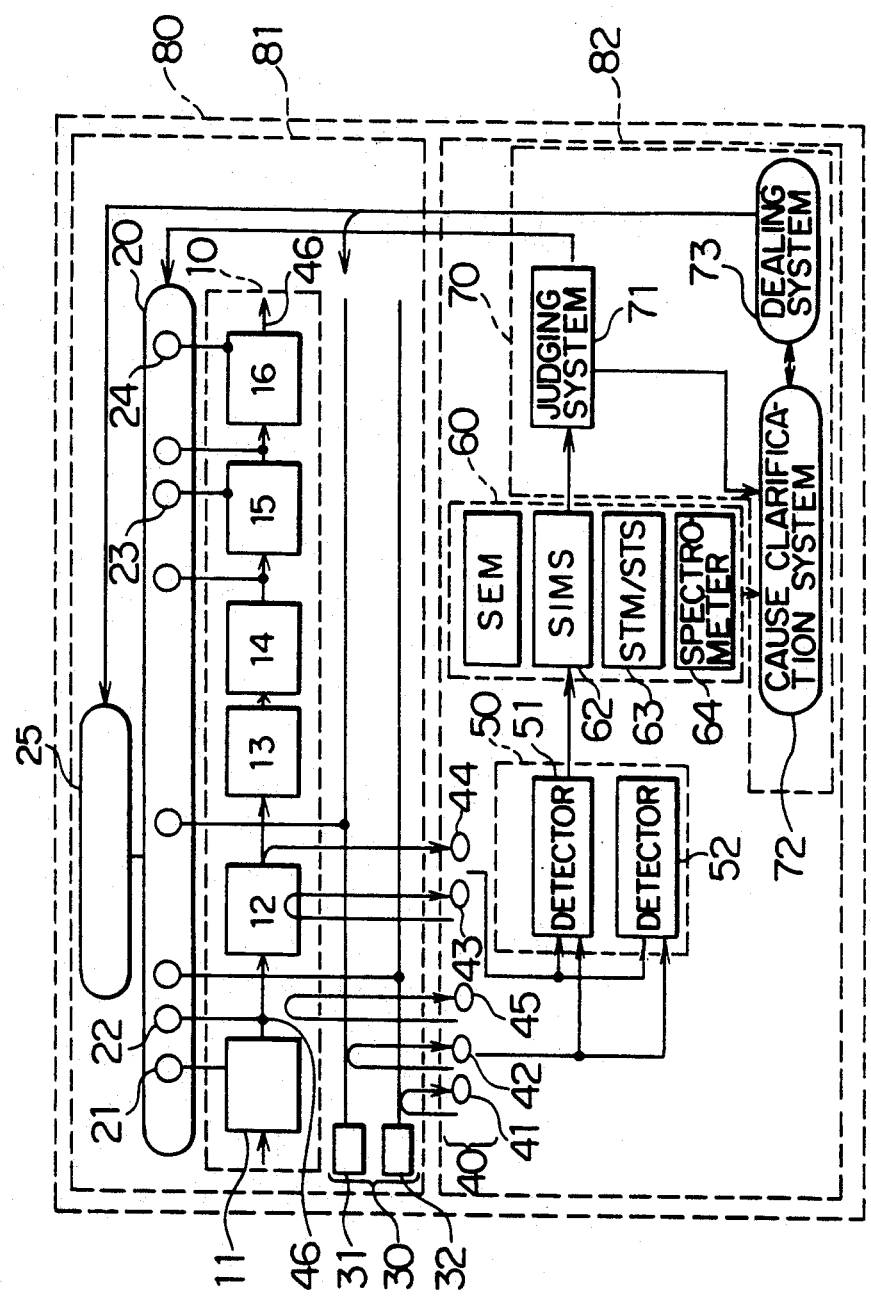
FIG. 1 is a structural block diagram of a foreign particle inspection method and apparatus during mass production start-up of a semiconductor fabrication process and in a mass production line according to an embodiment of the present invention.

FIG. 1 shows an embodiment of a method and apparatus for inspecting foreign particles during mass production start-up and in a mass production line in a semiconductor fabrication process.

In FIG. 1, a foreign particle inspection apparatus during mass production start-up and in a mass production line in a semiconductor fabrication process comprises a semiconductor fabrication apparatus group 10 including an exposure unit 11, an etching unit 12, a washing unit 13, an ion implantation unit 14, a sputtering unit 15, a CVD unit 16, etc.; a sensing unit 20 including a temperature sensor 21, a foreign particle monitor 22 inside a transfer system, a pressure sensor 23, a foreign particle monitor 24 inside a processing apparatus, etc.; a utility group 30 including a control system 25 for the sensing unit, a gas supplier 31 and a water supplier 32; a sampling unit 40 including a water quality sampling wafer 41, a gas sampling wafer 42, an in-unit sampling wafer 43, a device wafer 44, and an atmosphere sampling wafer 45; a detecting unit 50 including a wafer foreign particle detector 51 and a pattern defect detector 52; an analysis unit 60 including a scanning electron microscope (SEM) 61, a secondary ion mass spectrometer (SIMS) 62, a scanning tunneling microscope/spectrometer (STM/STS) 63 and an infrared spectrometer 64; and a dealing system 70 including a foreign particle criticality judging system 71, a fine foreign particle cause clarification system 72, and a contamination source dealing system 73. These constituent components are divided into an on-line foreign particle inspection system 81 corresponding to the mass production line and an off-line foreign particle inspection system 81 corresponding to the mass production start-up, and they altogether constitute the foreign particle inspection system 80 during the mass production start-up and in the mass production line in the semiconductor fabrication process.

Accordingly, because the state during the mass production start-up and the state in the mass production line are separated from each other as shown in the drawing, the apparatuses for detecting, analyzing and evaluating the foreign particles during the mass production start-up can be efficiently operated and the mass production start-up can be effected rapidly. At the same time, the foreign particle inspection and evaluation equipments used for the mass production line can be constituted by the minimum necessary simple monitors and the scale of the mass production line can be reduced.

Figure 2:
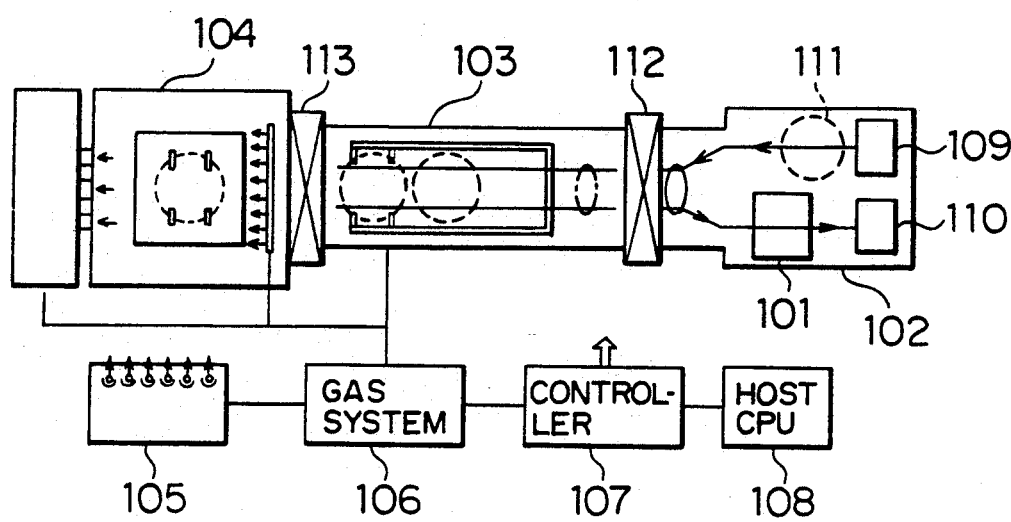
FIG. 2 is a plan view of a sheet type CVD apparatus to which a foreign particle monitor in an embodiment of the invention is mounted.

Next, an embodiment of the foreign particle monitor 22 inside the transfer system and the foreign particle monitor 24 inside the processing apparatus that are the on-line monitors of the on-line foreign particle inspection system 81 will be illustrated. FIG. 2 shows an application example of the foreign particle monitor 101 as the on-line monitor to the transfer system of the sheet type CVD unit 16 in which a particularly large number of defects occur among the semiconductor fabrication apparatus group 10. This CVD unit 16 comprises a loader 102 including the foreign particle monitor 101, a preparation chamber 103, a reaction chamber 104, a heating unit 105, a gas system 106, a controller 107 and a host CPU 180. Product wafers 111 are transferred from a loader cassette 109 placed in the loader unit 102 to the preparation chamber 103. The preparation chamber 103 is evacuated after a gate valve 112 is closed. Next, the gate valve 113 is opened and the product wafers 111 in the preparation chamber 103 and in the reaction chamber 104 are exchanged between them. After the gate valve 113 is closed, film formation is started in the reaction chamber 104. The internal pressure of the preparation chamber 103 is returned to the atmospheric pressure during the film formation. The gate valve 112 is then opened and the product wafers 111 are recovered. Any foreign particles on the product wafers 111 are inspected by the foreign particle monitor 101 during the transfer of the product wafers to an unloaded cassette 110. Alternatively the monitor 101 may be disposed just before the valve 112 in order to compare foreign particles on wafers before and after the film formation.

Figure 3:
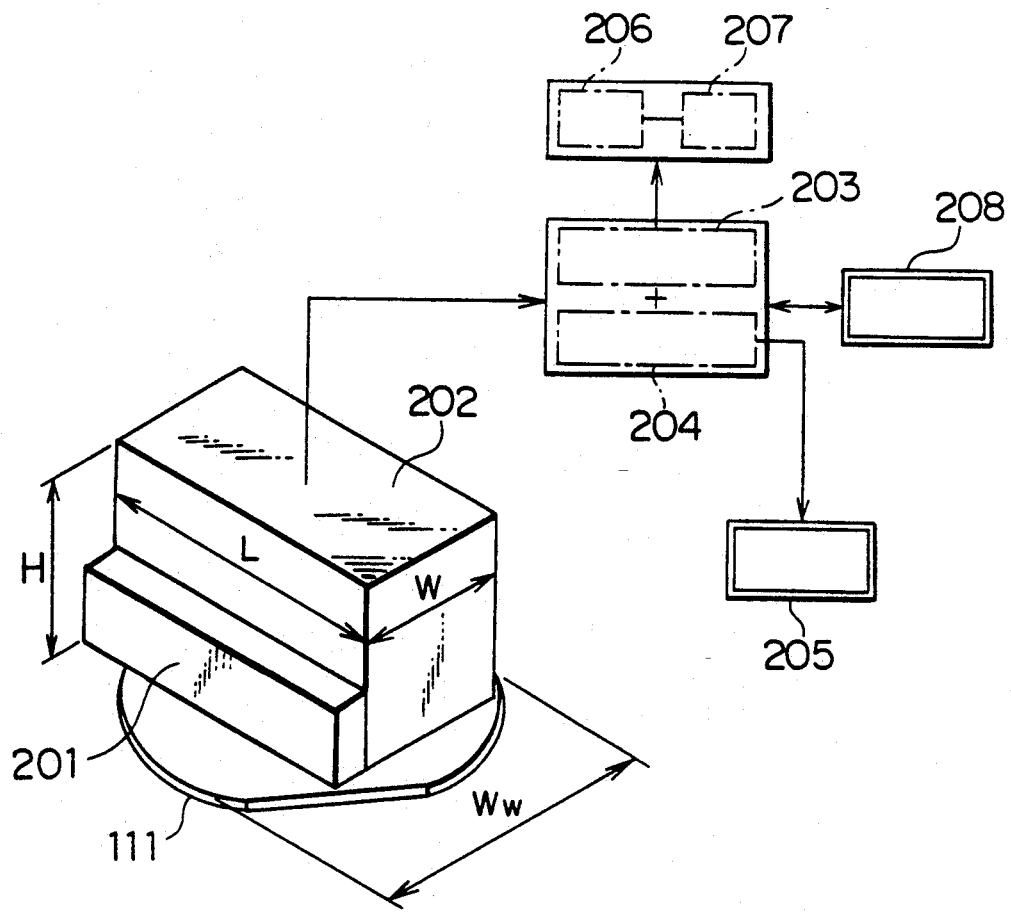
FIG. 3 is a structural view of the foreign pattern monitor.

Next, the construction of the foreign particle monitor 101 will be explained with reference to FIG. 3. To begin with, the direction of orientation flat of the product wafer 111 is detected by a wafer rotating direction detector 201 disposed on the foreign particle inspection start side of the foreign particle monitor 101 and the rotating direction of the product wafer 111 is detected. Next, the foreign particle inspection is effected on and throughout the entire surface of the product wafer 111 by a foreign particle detecting optical system 202. The foreign particle data obtained from the monitor 101 are processed by a foreign particle data processing system 203 and abnormal occurrence of the foreign particles, if any, is reported by an alarm, or the like. Alternatively, the operation of an apparatus main body 205 can be stopped by an apparatus stop function 204. Foreign particle display is effected by a keyboard 206 and a CRT 207. Furthermore, the foreign particle data processing system 203 is connected in the interlocking arrangement with a foreign particle analyzing system 208 and data exchange can be made between them. If a command of desired data such as the name, position, sampling, etc., of the product wafer 111 is transmitted from the system 208, for example, the desired data can be acquired from the system 203.

In this monitor 101, the foreign particle detection optical system 202 has a structure such that it is a separate member from the system 203, does not include a stage system and utilizes the transfer system of the processing apparatus. However, the monitor 101 may be course include the stage system. Accordingly, the outer dimension of the monitor 101 is up to 1 m in width W, depth L and height L, or the width of the monitor 101 is smaller than that w of the wafer. Accordingly, the monitor 101 can be made compact in scale. The monitor 101 has an automatic calibration function, can automatically measure the reflective indices because the refractive indices on the product wafers vary between the production equipments and between the production steps, feeds back the refractive indices to the illumination light power of the foreign particle detecting optical system and thus eliminates the necessity for troublesome calibration. Furthermore, the depth of focus d of the detecting lens is calculated from the following formula and is as deep as 0.1 to 0.5 mm. Accordingly, automatic focusing is not necessary.

$$d = 0.5\lambda/(NA)^2 \quad (1)$$

where $\lambda$ is the wavelength of light and NA is numerical aperture of the detecting lens. Because the system 202 is compact, unit exchange is possible and its mounting and setting to the apparatus is easy. Furthermore, maintenance is easy, as well.

Figure 4:
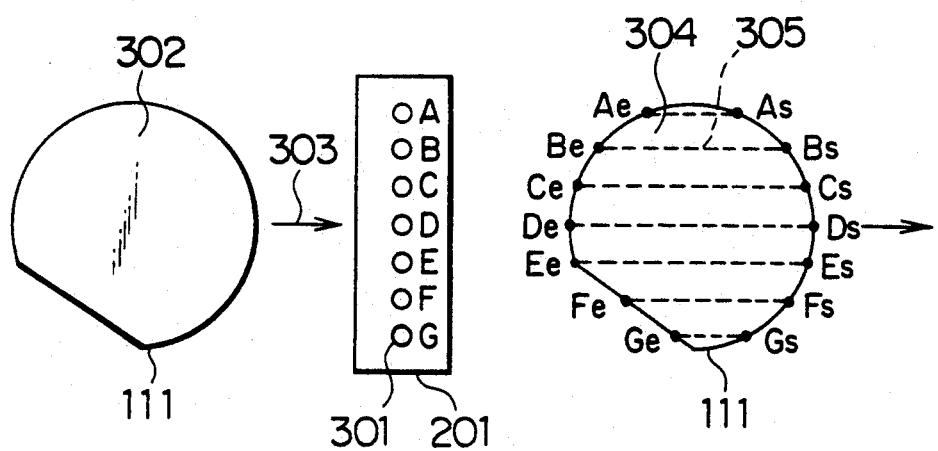
FIG. 4 is a drawing showing a detection method of a wafer rotating direction detector.

The detection method of the wafer rotating direction detector 201 will be explained with reference to FIG. 4. The product wafer 111 passes in the wafer moving direction 303 below an illumination system having several or more illumination points 301 and moves from the position 302 to the position 304. The drawing shows the trajectory 305 of the illumination light outgoing from the illumination point of the illumination system of the wafer rotating direction detector 21 on the product wafer 111. In the case of the illumination point A, for example, the time As in which the illumination light illuminates the product wafer 111 and the time Ae in which the light is off from the product wafer 111 are measured, and these procedures are likewise carried out for the other illumination points B to G. The direction of orientation flat of the product wafer 111 is determined on the basis of the data described above and of the moving time of the product wafer 111, and the rotating direction of the product wafer 111 is calculated. The detection method of the rotating direction of the product wafer 111 includes specific mark detection such as scribe area detection, chip detection, alignment mark detection, and so forth.

Figure 5:
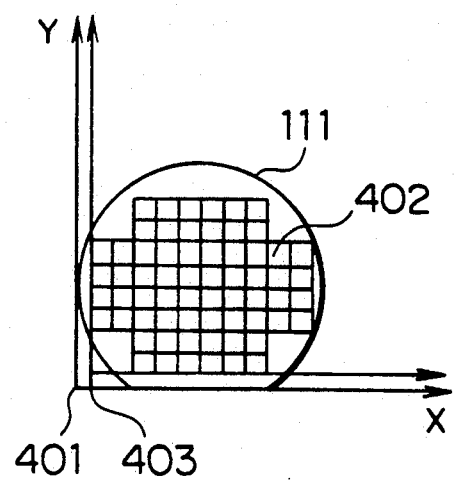
FIG. 5 is a drawing showing the coordinates of a product wafer standard for foreign particle coordinates management.
Figure 6:
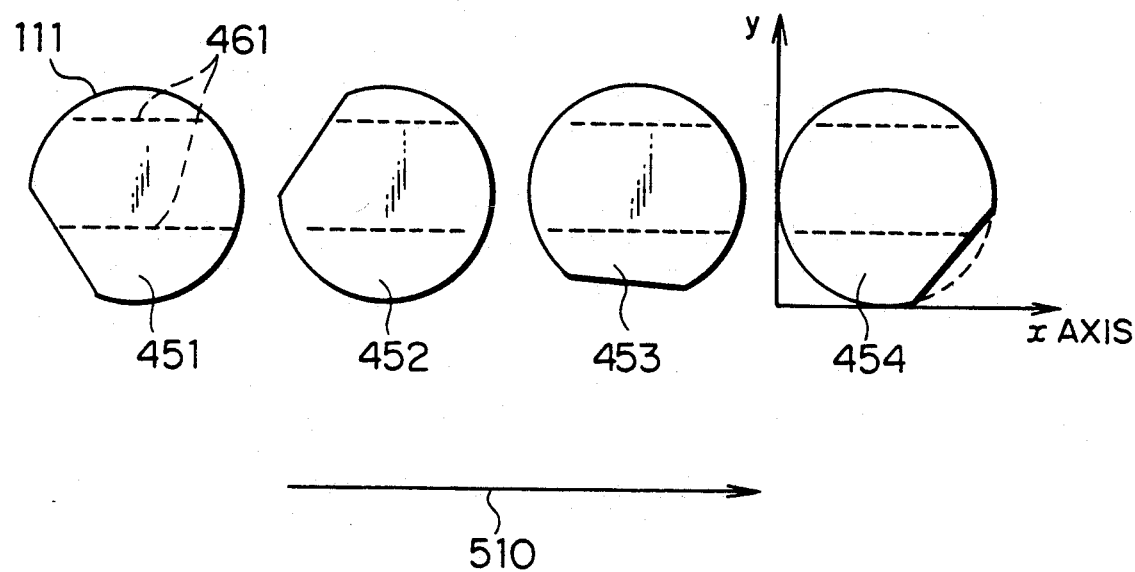
FIG. 6 is a drawing showing the coordinates of an apparatus standard for foreign particle coordinates management.

Accordingly, this foreign particle monitor 101 can make foreign particle coordinates management capable of obtaining the data of the positions of the foreign particles by means of the rotating direction of the product wafer 111 obtained by the wafer rotating direction monitor 201 and the coordinates of the orientation flat reference using the point of intersection between the extension X axis of the orientation flat and the Y axis crossing orthogonally the X axis and circumscribed with the outer periphery of the product wafer 111 as an imaginary origin 401 or the coordinates of a circuit pattern 402 reference using the point of intersection between the extensions of the circuit pattern 402 as shown in FIG. 5.

To know the dust generation distribution inside the apparatus, the foreign particle monitor 101 has the foreign particle coordinates management by the apparatus reference which comprises the x axis on which the transfer direction 510 and the outer periphery of each product wafer 111 come into mutual contact and the y axis which orthogonally crosses the x axis and comes into contact with the outer periphery of the product wafer 111, as represented by 454, and which does not rely on the rotating direction of the product wafer 111 even when the product wafers 111 are transferred with various rotating directions 451, 452, 453, 454. If dust generation occurs inside the apparatus, a regular foreign particle distribution is exhibited as represented by 461.

Furthermore, the wafer rotating direction detector 201 of the monitor 101 can detect the rotating direction of the product wafer 111 and at the same time, can determine the transfer speed of the product wafer 111. Therefore, the scan speed of the detector such as a CCD linear sensor, for example, can be changed in synchronism with the transfer speed of the product wafer 111. Accordingly, stable detection performance can be acquired irrespective of the transfer speed of the product wafer 111.

Figure 7:
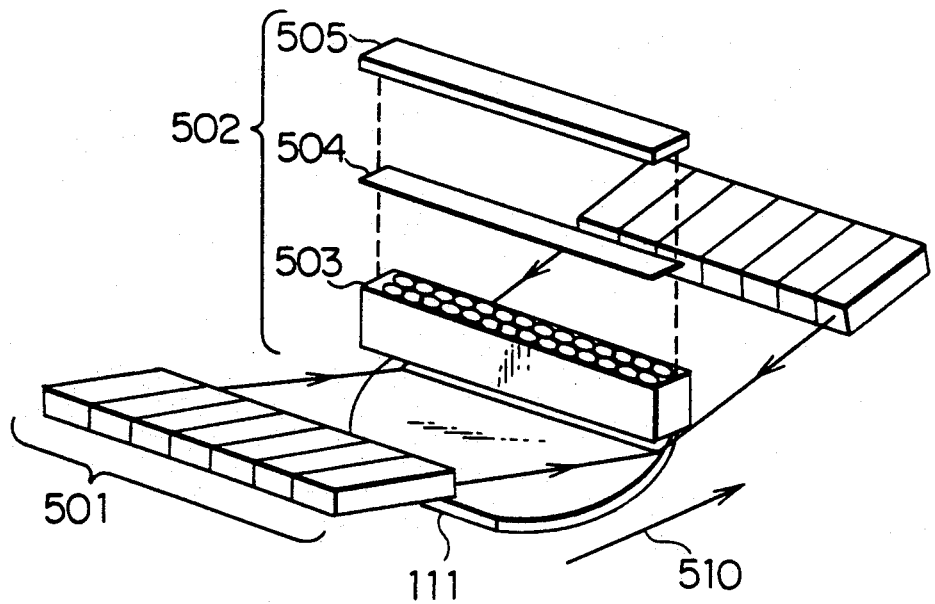
FIG. 7 is a structural view of a foreign particle detecting optical system.

FIG. 7 shows an embodiment of the foreign particle detecting optical system 202 using a spatial filter which can make foreign particle inspection on the product wafer 111 at a high speed and is compact in scale. It comprises an oblique illumination optical system 501 and a detecting optical system 502. The oblique illumination system 501 comprises at least one illumination array. The detecting optical system 502 comprises a lens array 503 as a detecting lens, spatial filters 504 on a Fourier transform plane of the lens array and a detector 505 at an imaging position of the lens array.

Figure 8:
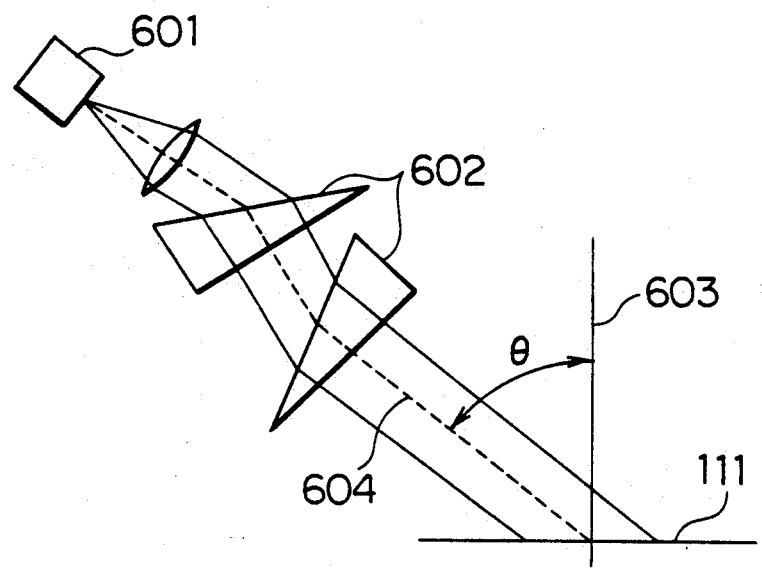
FIG. 8 is a structural view of an oblique illumination optical system.

FIG. 8 is a structural view of the oblique illumination optical system 501. Here, the term "oblique illumination" means illumination from a direction 604 inclined at an angle $\theta$ from the normal 603 of the product wafer 111. A compact and high output semiconductor laser 601 is used as the light source and an anamorphic prism 602 insures high luminance coherent illumination. When coherent illumination is made on the product wafer 111, a sharp Fourier transform image of the pattern of the product wafer 111 can be obtained on the Fourier transform plane of the detecting lens 503. In addition, the anamorphic prism 602 insures wide range illumination which is not affected by adjacent illumination components of the illumination array. If any influences of the adjacent illumination light exist, the Fourier transform image of the pattern is collapsed and overlaps due to the adjacent illumination, so that the area of the Fourier transform plane increases and the area of the filter portion of the spatial filter increases, as well. For this reason, the quantity of scattering light from the foreign particles passing through the spatial filter becomes smaller and the foreign particle detection performance drops.

Figure 9:
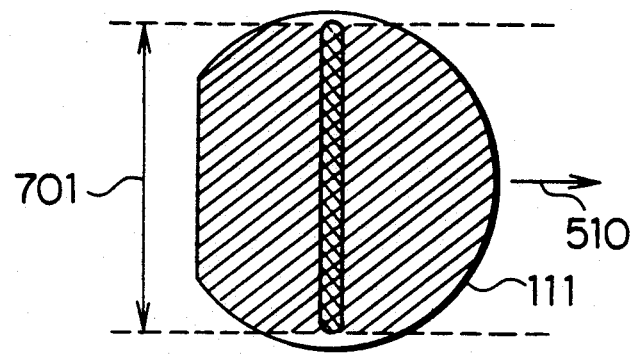
FIG. 9 is a drawing showing a detection width of a detecting optical system.

FIG. 9 shows the detection width of the detecting optical system 502. The detection width 701 of the detecting optical system 502 is the same as the width of the product wafer 111, and the entire surface of the product wafer 111 can be inspected in a lump by one scan 510 of a feed 510 of the product wafer 111, and high speed inspection becomes possible.

Figure 10:
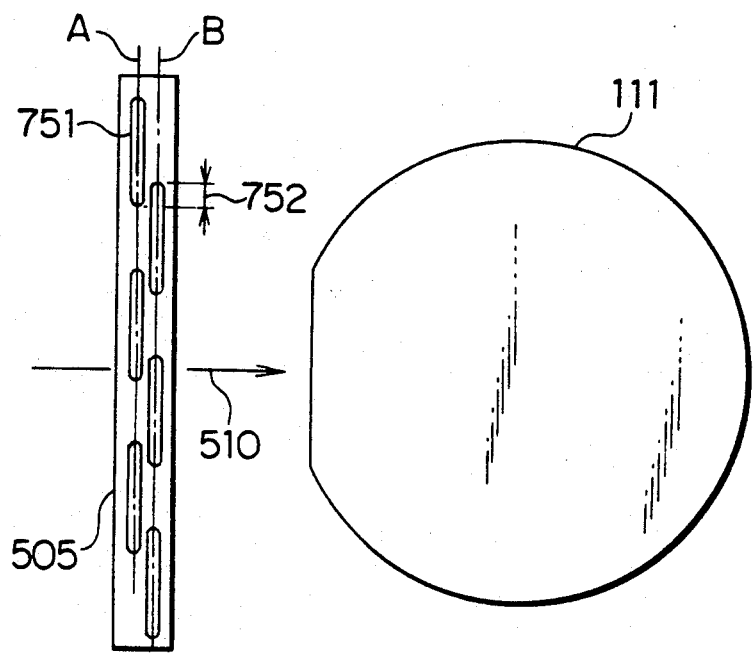
FIG. 10 is a structural view of a detector.

FIG. 10 shows the case where a CCD linear sensor is used as the detector 505. To detect the width of the product wafer 111 in a lump, a plurality of CCD linear sensors 751 are arranged zigzag as shown in the drawing. Line B is omitted at the portion 752 where the sensors overlap with each other, and the data of the line A are used as effective data.

Figure 11:
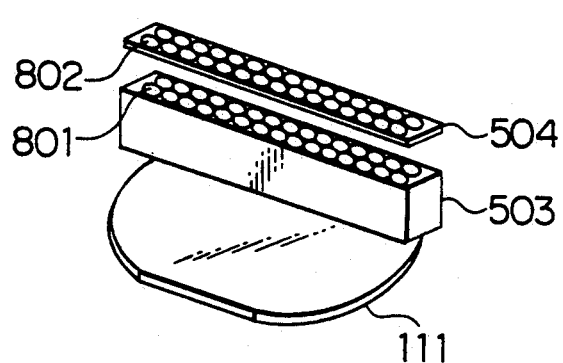
FIG. 11 is a structural view of a spatial filter.

FIG. 11 shows a structural view of the spatial filters 504. Each spatial filter 802 corresponds to each lens device 801 of the lens array 503.

Figure 12:
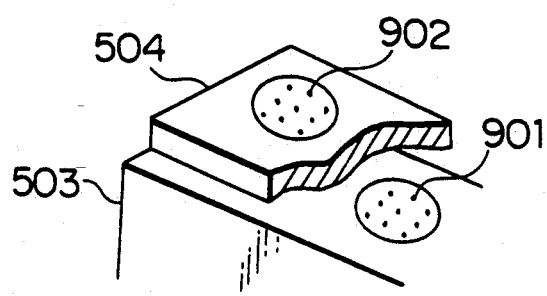
FIG. 12 is a detailed view of the spatial filter.

FIG. 12 is a detailed view of the spatial filter 504. The diffraction light 901 from the repetition pattern having regularity from the product wafer 111 becomes a regular image 902 at the position of the spatial filter 804 on the Fourier transform plane of the lens array 503. Therefore, the spatial filter 504 such as shown in the drawing can block the repetition pattern of the product wafer 111 having regularity, and the pattern is not taken into the CCD linear sensor 505 as the detector.

A dry plate type spatial filter which prints the Fourier transform image of the repetition pattern of the product wafer 111 on a dry plate is used as the spatial filter 504. Therefore, the printed portion of the spatial filter 504 does not pass the light from the repetition pattern of the product wafer 111 having regularity. Alternatively, a liquid crystal type spatial filter using a liquid crystal may be used. First of all, the regular image 902 at the position of the spatial filter 504 on the Fourier transform plate of the lens array 503, formed by the diffraction light 901 from the repetition pattern of the product wafer 11 having regularity, is detected by a TV monitor, or the like, and the positions of liquid crystal devices corresponding to this image 902 are stored. Next, a voltage is applied to the liquid crystal device portions thus stored, and in this way, the light striking these portions can be blocked. Accordingly, a spatial filter by means of ON/OFF of the liquid crystal devices for each product wafer at each production step can be constituted by storing the liquid crystal devices corresponding to the images for each product wafer at each production step and formatting them.

Figure 13:
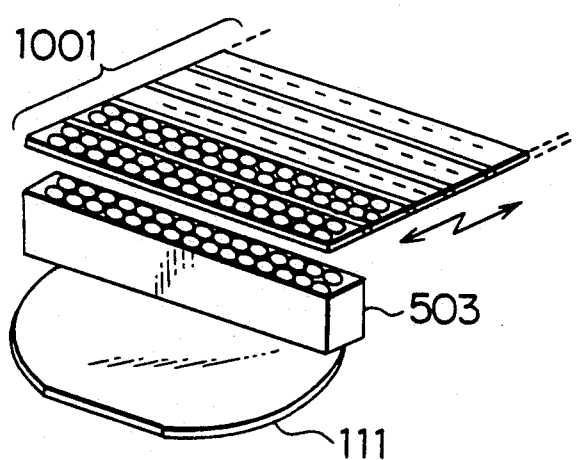
FIG. 13 is a structural view of a spatial filter group by a dry plate system corresponding to a product wafer at each production step.

FIG. 13 shows a group of spatial filters 1001 by a dry plate system corresponding to the product wafer 111 at each production step. A spatial filter corresponding to the product wafer 111 at each production step is produced by a dry plate system, is exchanged by a moving mechanism such as a linear guide stage as shown in the drawing and is positioned relative to the detecting lens 503. In this manner, the spatial filters can be so arranged as to correspond to the product wafers 111 at all the production steps.

Figure 14:
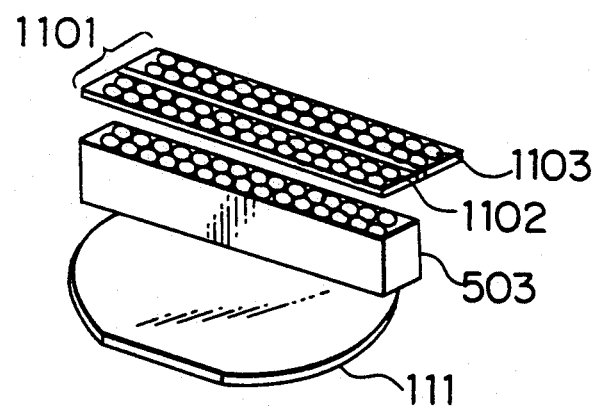
FIG. 14 is a structural view of an AND spatial filter by a dry plate system.

FIG. 14 shows an AND spatial filter 1101 by a dry plate system. The number of the spatial filters can be reduced by effecting an AND operation between the spatial filters for several kinds of production steps, and the light from the repetition pattern of the product wafers 111 of several kinds of production steps can be blocked by a single AND spatial filter 1102. When the AND spatial filter 1101 is used, therefore, the number of the spatial filters can be reduced even when the number of production steps is great, and the construction of the equipment can be simplified. In addition, this method can be applied to the spatial filters of the liquid crystal system and the number of formats can be reduced, as well. It is possible, in principle, to use only one AND spatial filter by effecting the AND operation between the spatial filters of all the production steps, but foreign particle detection performance drops in this case because the quantity of scattering light from the foreign particles patting through the AND spatial filter becomes smaller.

Figure 15:
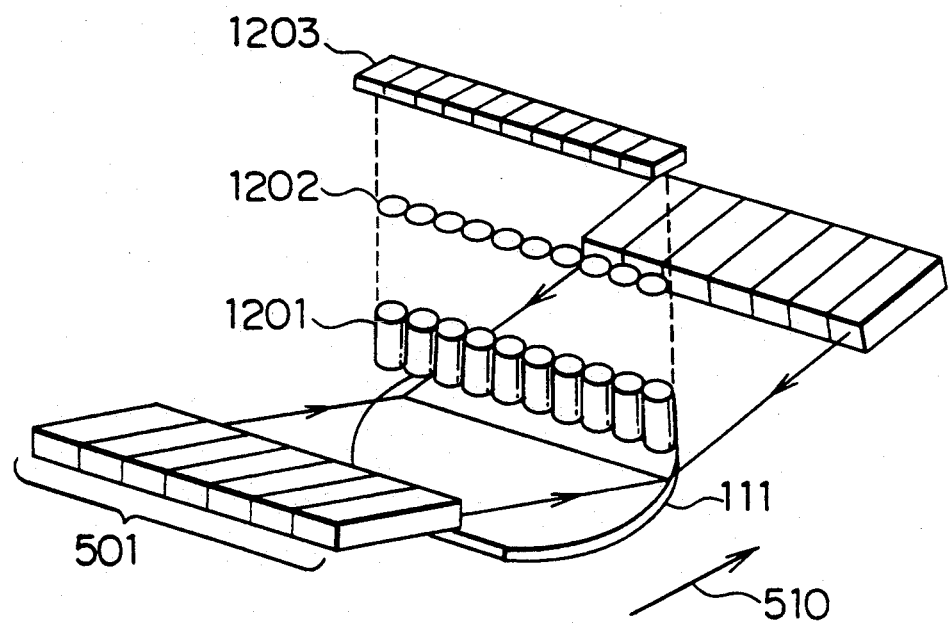
FIG. 15 is a structural view of a foreign particle detecting optical system by partial inspection.

Next, FIG. 15 is a structural view showing an embodiment of the foreign particle detecting optical system 202 by partial inspection. A microlens group 1201 is used as the detecting lens and the spatial filter 1202 is disposed on the Fourier transform plane of each microlens 1201. Furthermore, each CCD linear sensor 1203 is disposed as the detector. Foreign particles having smaller dimensions can be detected by using the microlenses 1201 having higher resolution than by using the lens array 503. In this system, however, inspection can of course be made by the use of the conventional lens in place of the microlenses 1201 as the detecting lens. The inspecting range can be made effective by aligning the pitch of the microlens group 1201 with the chip of the product wafers as an embodiment of partial inspection.

Figure 16:
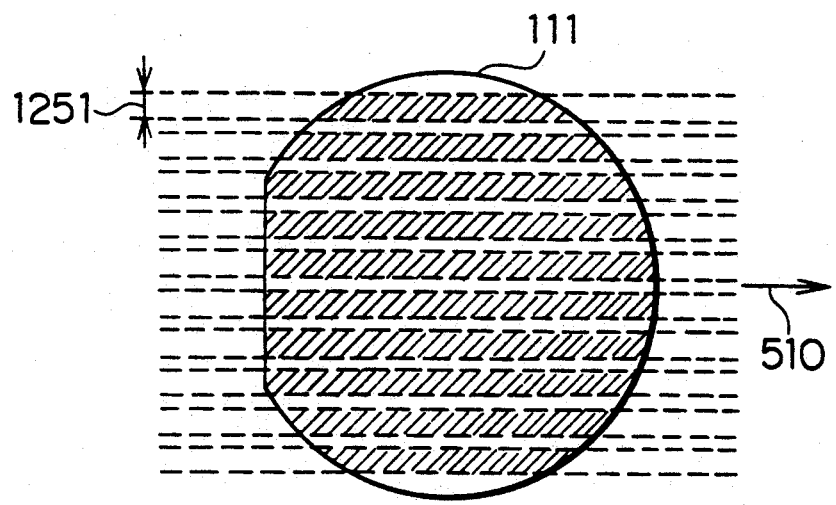
FIG. 16 is a drawing showing a detection area of the foreign particle detecting optical system by partial inspection.
Figure 17:
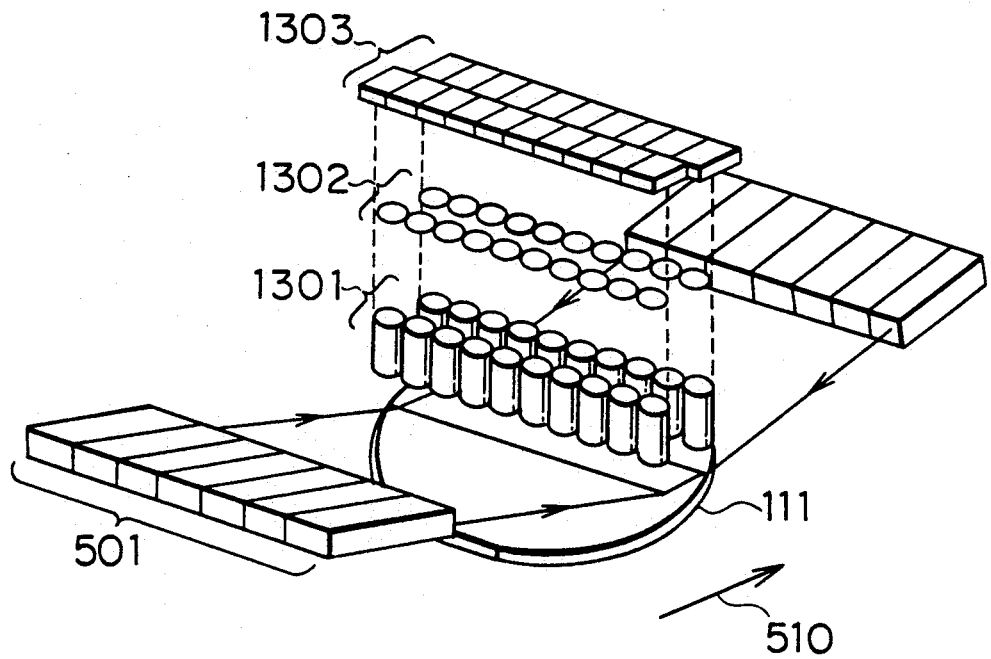
FIG. 17 is a structural view of the foreign particle detecting optical system by a microlens system of lenses arranged in two rows.

As represented by hatched portions in FIG. 16, however, the inspection on the product wafer 111 becomes a partial inspection when only one line of the microlens group 1201 is used. Though the monitor function of the foreign particles can be exhibited in this case, the inspection of the entire surface of the product wafer 111 cannot be made. Here, reference numeral 1251 represents a detection width of one microlens 1201. When the product wafer 111 is scanned many times, the entire surface of the product wafer 111 can be inspected. Alternatively, the full surface inspection of the product wafer 111 can be made by one scanning 510 by disposing two or more lines of microlenses 1301 in a zigzag arrangement as shown in FIG. 17.

As another embodiment in FIG. 15, wide range and high luminance illumination is made on the product wafer 111 using a pulse light emission laser as the oblique illumination system 501. Furthermore, when a two-dimensional CCD sensor or a TV camera 1203 is used as the detector, detection can be made over a wide range. When pulse light emission is effected in the oblique illumination system 501, the detector is synchronized with illumination for detection.

Figure 18:
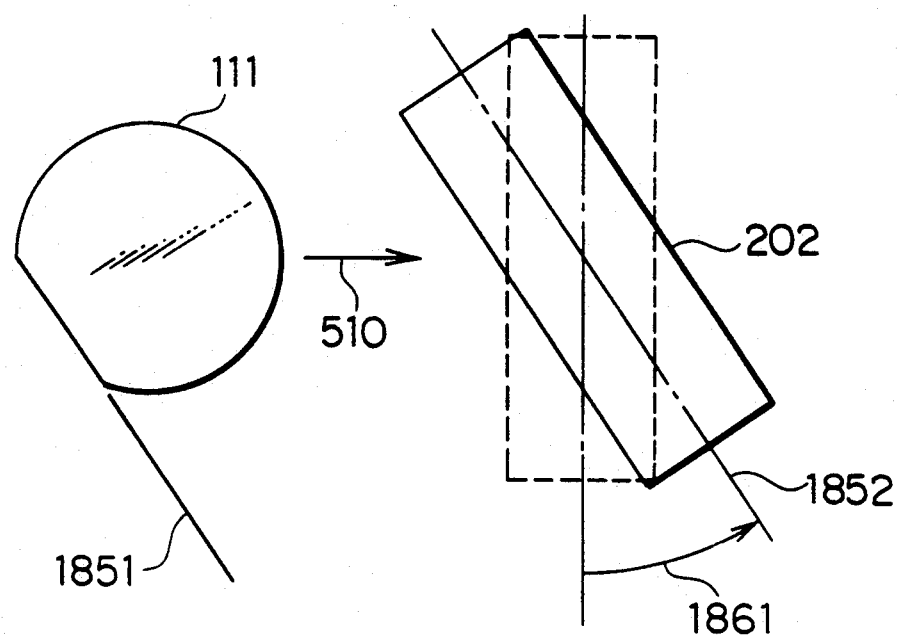
FIG. 18 is a drawing showing a spatial filter detection method by the rotation of a wafer when a lens array is used.

When the spatial filter is used in the embodiment described above, an orientation flat positioning mechanism is disposed at an intermediate position of the transfer system of the apparatus in such a manner as to align the direction of the product wafer 111 with the direction of the spatial filter. In this way, the spatial filter detection becomes possible. When the product wafers 111 are being transferred with various rotating directions, however, the direction of the repetition patterns of the product wafers 111 changes, too, so that the spatial filter must be rotated in match with the rotating direction of the product wafer 111. When the microlenses shown in FIGS. 15 and 17 are used, the adjacent spatial filters are independent of each other. Therefore, the individual spatial filters may be rotated in match with the rotating direction of the product wafers 111. When the lens array is used, however, the adjacent spatial filters are continuous, so that the foreign particle detecting optical system 202 must be rotated as represented by reference numeral 1861 in the direction represented by reference numeral 1582 in match with the rotating direction 1851 of the product wafer 111 as shown in FIG. 18. Needless to say, the foreign particle detecting optical system 202 may be rotated in match with the rotating direction 1851 of the product wafer 111 when the microlens is used, as well. Here, the direction 1851 is the same as the direction 1852. The angle of rotation is maximum 45°, and the detection width becomes greater with the rotation in the case of FIG. 18.

When the spatial filter is used, the inspection of the regular repetition pattern portion on the product wafer 111 can be made but the inspection of the other portions cannot be made. Accordingly, the portions other than the regular repetition pattern portion on the product wafer 111 are made to be inefficient data area or detection inhibition area by a software. In this case, spots on the product wafer 111 is monitored at a specific ratio without monitoring the foreign particles on all the points on the product wafer 111, and monitoring of only the repetition portion of a memory provides a great effect in the case of the fabrication of memories having a large number of repetition patterns.

Figure 19:
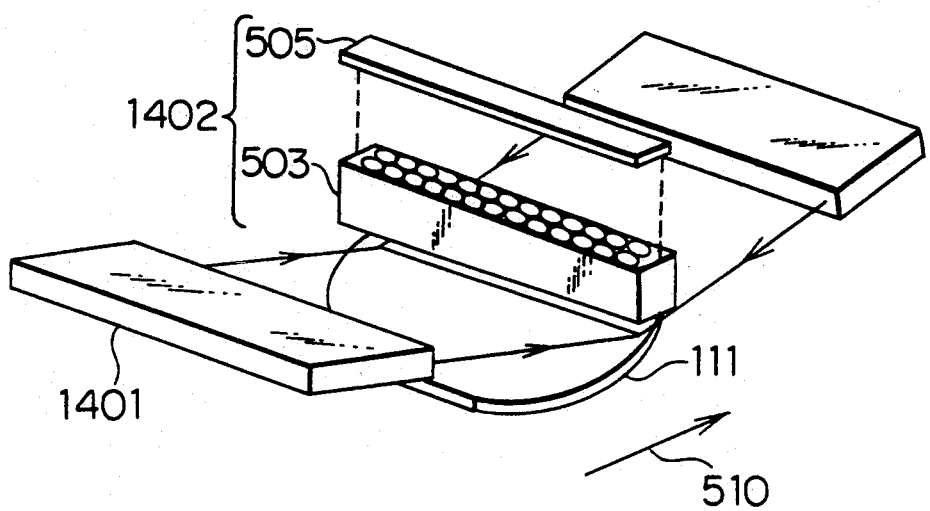
FIG. 19 is a structural view of the foreign particle detecting optical system by white light illumination.
Figure 20:
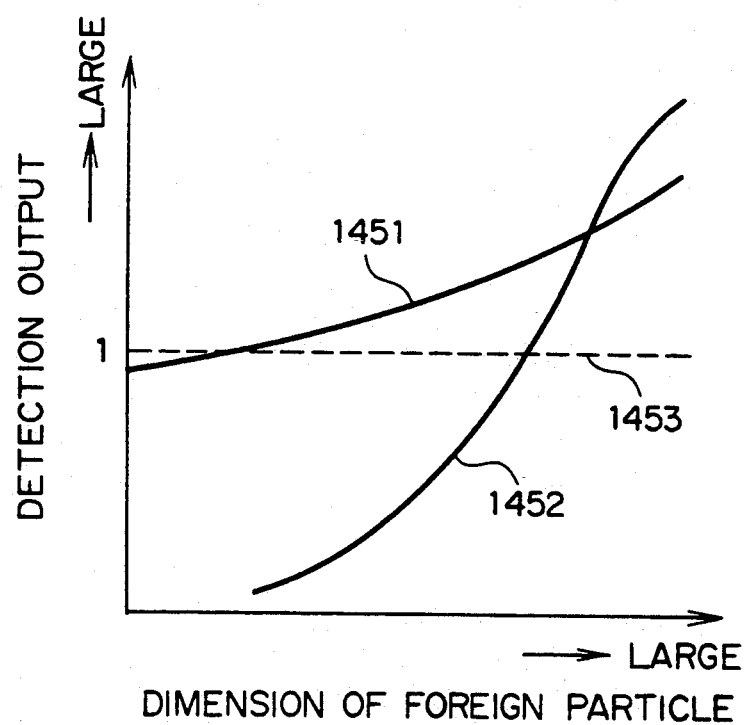
FIG. 20 is a diagram showing foreign particle detection performance by white light illumination.

Next, FIG. 19 is a structural view showing an embodiment of the foreign particle detecting optical system 202 by white light illumination. The system comprises an oblique illumination system 1401 by white light and a detecting optical system 1402 which in turn comprises a lens array 503 and a detector 505. According to this system, foreign particle detection performance becomes lower than the spatial filter system. Nonetheless, white light illumination detection 1451 has higher detection performance than laser illumination detection not using the spatial filter as shown in FIG. 20 and can inspect the full surface of the product wafer 111 without being limited to its regular repetition pattern. In this diagram, the detection output from the foreign particle is plotted with the peak value of all the patterns on the product wafer 111 as the reference 1453.

Figure 21:
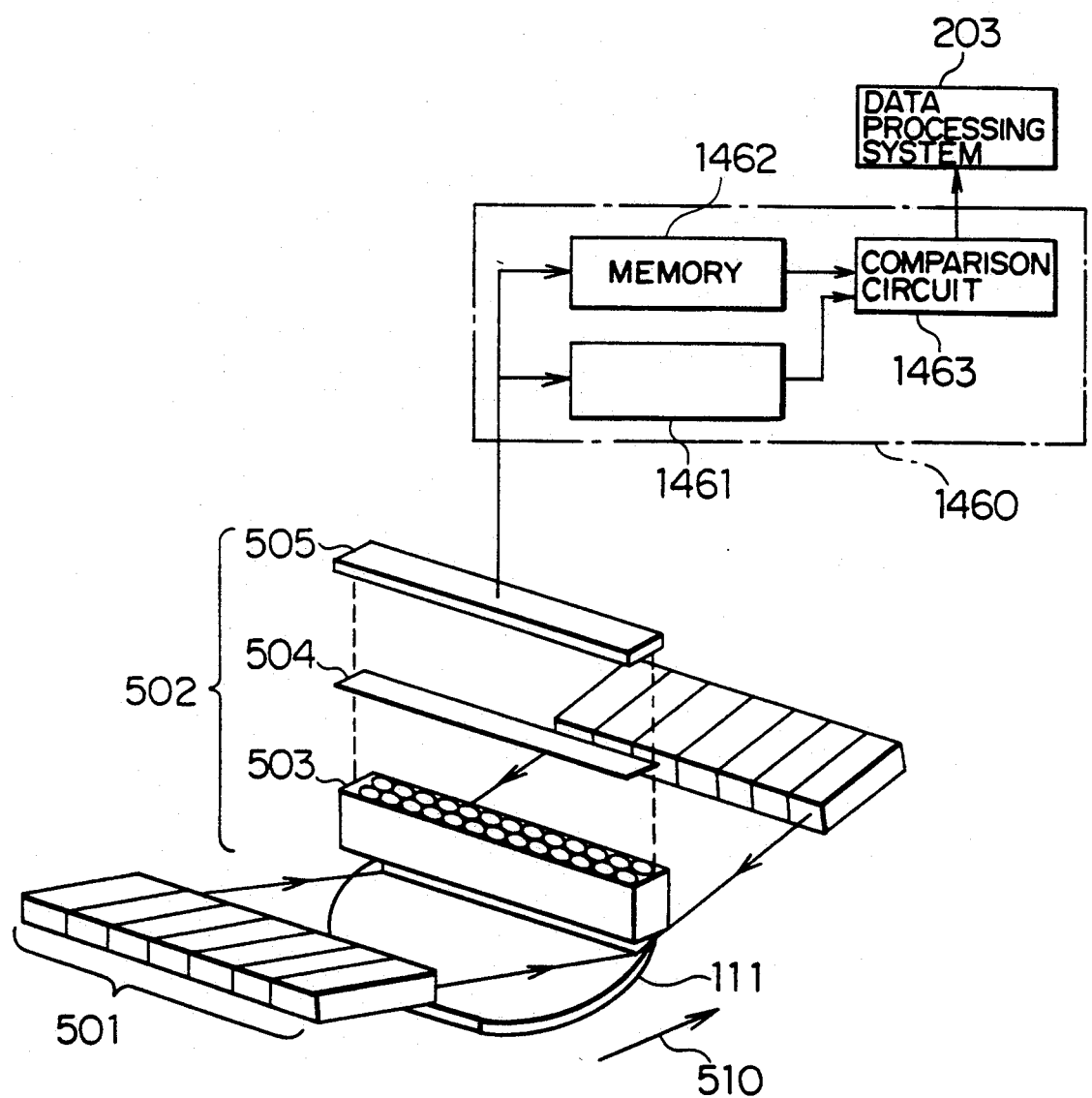
FIG. 21 is a structural view of the foreign particle detecting optical system by wafer comparison inspection.

FIG. 21 is a structural view showing an embodiment of the foreign particle detecting optical system by a wafer comparison inspection. The system comprises an oblique illumination optical system 501 and a detecting optical system 502. The oblique illumination optical system 501 comprises at least one illumination array as shown in the drawing. The detecting optical system 502 comprises a lens array 503 or a microlens group as the detecting lens, a spatial filter 504 disposed on the Fourier transform plane of the detecting lens 503, a detector 505 disposed at an imaging position of the detecting lens 503 and an image processing system 1460 for image-processing the detection signal from the detector. To begin with, the first product wafer 111 is detected and is stored as an image in a memory 62. Next, the memory image 1462 of the first product wafer 111 and a second memory image 1461 of the second product wafer 111 are compared by a comparison circuit 1463 in order to actualize the existence of any foreign particles. The detection images of the third et seq product wafers 111 are compared with the memory image of the first, second or preceding product wafer 111. In this embodiment, the pattern data are reduced by the use of the spatial filter 504. Therefore, the orientation flat positioning mechanism, or the like, is disposed before the detection by the foreign particle detecting system, and the rotating directions of all the product wafers 111 are brought into conformity with the rotating direction of the spatial filter.

Figure 22:
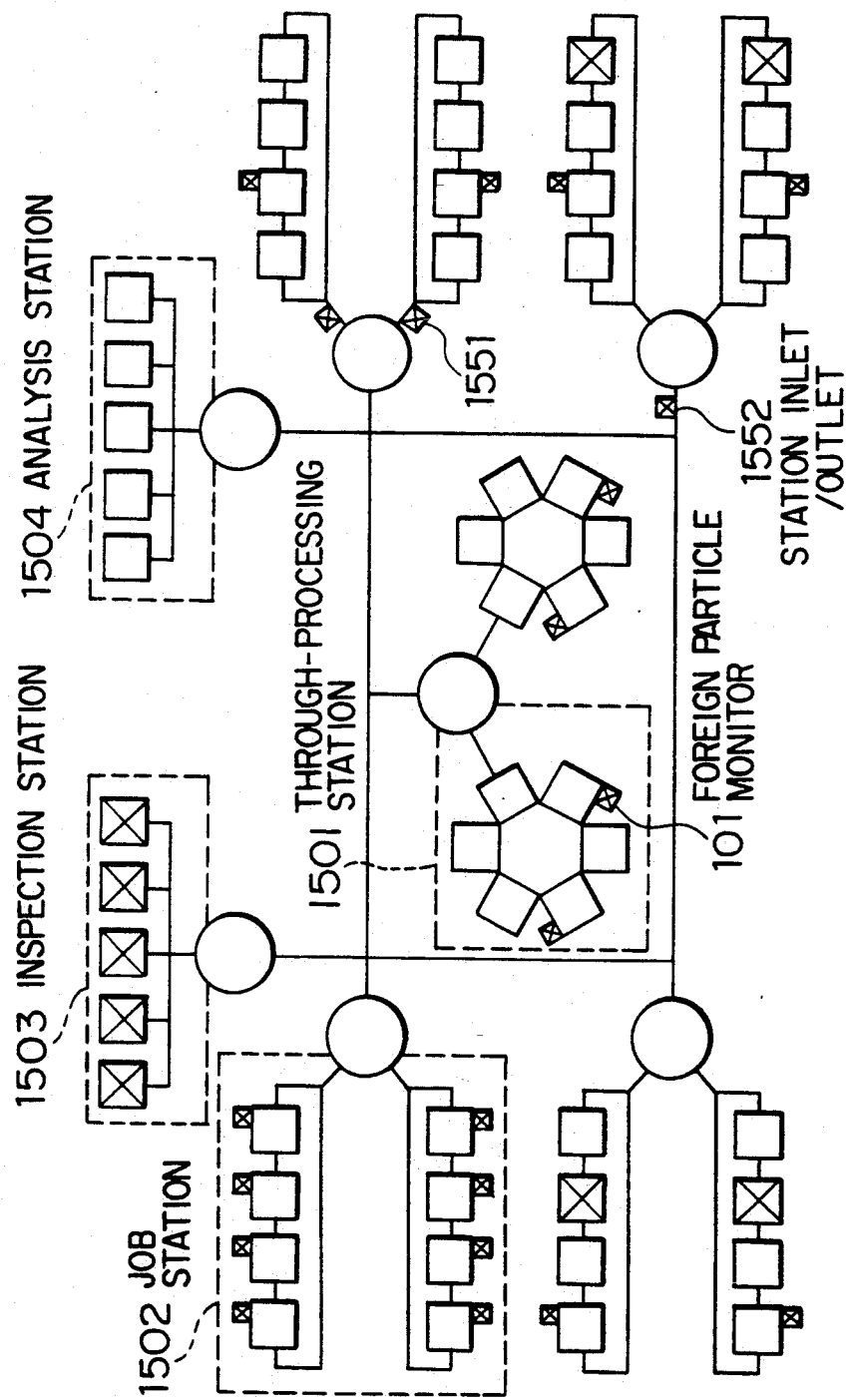
FIG. 22 is a system diagram of a semiconductor FA using a foreign particle monitor.

FIG. 22 is a system diagram of semiconductor FA (Factory Automation) using the foreign particle monitor 101. The system comprises a through-processing station 1501 capable of through-processing the product wafers 111, various jobs stations 1502 corresponding to various specific processings, an inspection station 1503 and an analysis station 1504. Each station is connected by a transfer system inside a clean tunnel. The foreign particle monitors 101 are mounted to CVD apparatuses and etching apparatus, where there is a particularly high possibility of occurrence of a large number of defects, in the through-processing station 1501 and in the various jobs station 1502, in order to monitor the foreign particles inside these apparatuses. The foreign particle monitors 101 are mounted also to the transfer system at the inlet and outlet of the stations such as represented by 1551 and 1552. The above-mentioned aspect of the present invention is preferably applied to monitoring of the mass production line on start-up of the line.

According to the present invention, the production line can be simplified and the production cost can be reduced by monitoring the foreign particles by the easy-to-use monitors in the mass production line of the semiconductor fabrication process. Furthermore, since the monitors can make sampling on the real time basis, they can prevent in advance mass defects which would otherwise be very critical to the yield, and can provide the effect of stably securing the yield.

Hereinafter, definite embodiments of the foreign particle monitors of the present invention will be explained with reference to FIGS. 23 to 32.

The construction of this embodiment will be explained with reference to FIG. 23. This embodiment comprises an illumination optical system 101 comprising a semiconductor laser 111, a collimator lens 112, an x diffusing lens 113, a convergent lens 114, a y diffusing lens 115 and a mirror 116; a detecting optical system 201 comprising an imaging lens 211, a spatial filter 212, a deflector 213 and a unidimensional detector 214; a stage system 301 comprising wafer transfer means 311, an automatic focusing detector 312 and an automatic focusing-positioning mechanism 313; a signal processing system 401 comprising an A/D convertor 411, a threshold value circuit 412, a two-dimensional image segmentation circuit 413, a pattern foreign particle judgement circuit 414, a pattern data memory 415 and a foreign particle data memory 416; and a data processing system 501 comprising an FFT circuit 511, a repetition portion elimination circuit 512, a data memory 513, a microcomputer 515, a data display system 516 and an abnormality display alarm 517.

In the illumination optical system, the beam emitted from he semiconductor laser 111 is converted to a plane wave by the collimator lens 112, and only the x direction is expanded by the x diffusing lens 113. The beam leaving the x diffusing lens 113 is converted to parallel luminous fluxes or in other words, the plane waves, in the x direction, and is converged in the y direction, by the convergent lens 114. Therefore the beams in only the y direction are diffused to the parallel luminous fluxes by the y diffusing lens. After all, the beams are the parallel luminous fluxes in both the x and y directions or the plane waves, become a beam on the elongated line in the y direction and illuminate the wafer 1.

Figure 24:
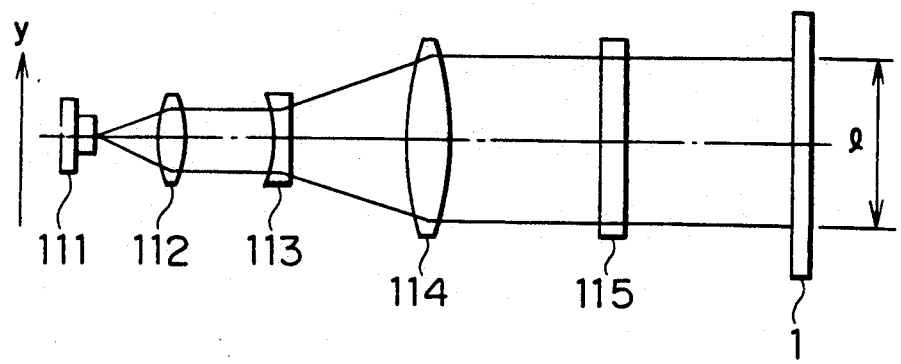
FIG. 24 is a side view of an illumination optical system when viewed from an x direction.
Figure 25:
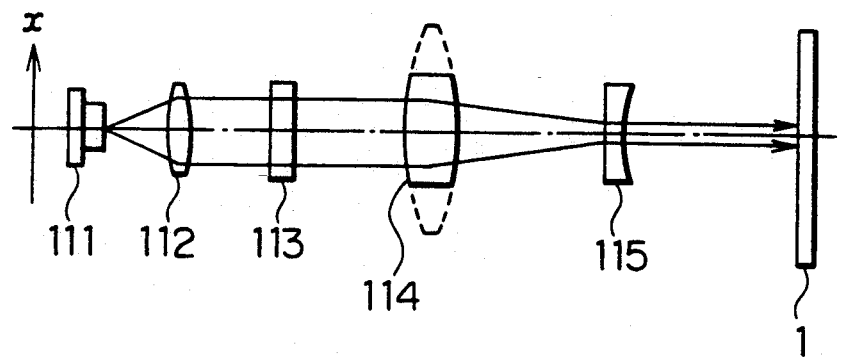
FIG. 25 is a side view of the illumination optical system when viewed from a y direction.

FIG. 24 shows the structure of the illumination optical system 110 when viewed from the x direction and FIG. 25 shows the structure when viewed from the y direction. The beam expands in the y direction such that it can sufficiently illuminate the illumination area, but is contracted in the x direction to provide sufficient illumination. However, this illumination is the plane waves or in other words, the parallel luminous flux in each of the x and y directions.

In this embodiment, illumination is made by converting the beam to the parallel luminous fluxes or the plane waves in both the x and y directions, but the optical system may be sufficiently such that it provides approximately plane waves. Here, plane polarized light is irradiated so that a magnetic field vector is perpendicular to the incidence surface of the illumination. In this manner, scattering light from the foreign particles can be improved relatively to scattering light from the patterns. The polarized light need not always be the s polarized light and the object of the invention can be accomplished sufficiently by other polarized light such as linearly polarized light, elliptically polarized light, circularly polarized light, or the like.

In the detecting optical system 210, the imaging lens 211 forms the image of the luminous flux emitted from the inspection position 2 on the wafer 1 on the unidimensional detector 214 through the spatial filter 212 and the deflector 213. In the deflector 213, the magnetic field vector blocks the light (S polarized light) perpendicular to the incidence surface of the illumination. This deflector provides the effect of relatively improving the scattering light from the foreign particles to the scattering light from the patterns. However, the deflector is not always necessary, and the object of the present invention can be sufficiently accomplished without using the deflector.

Figure 26:
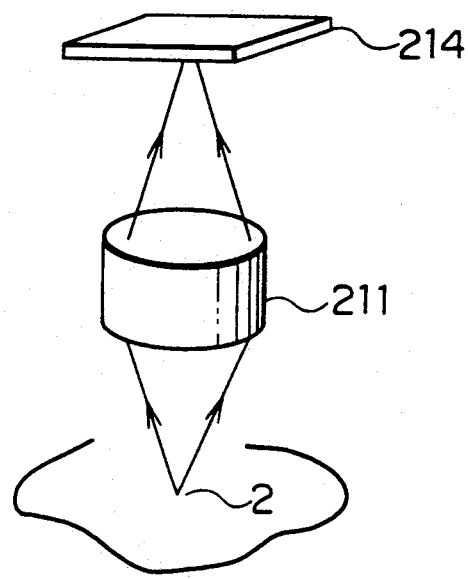
FIG. 26 shows an example of an imaging lens.
Figure 27:
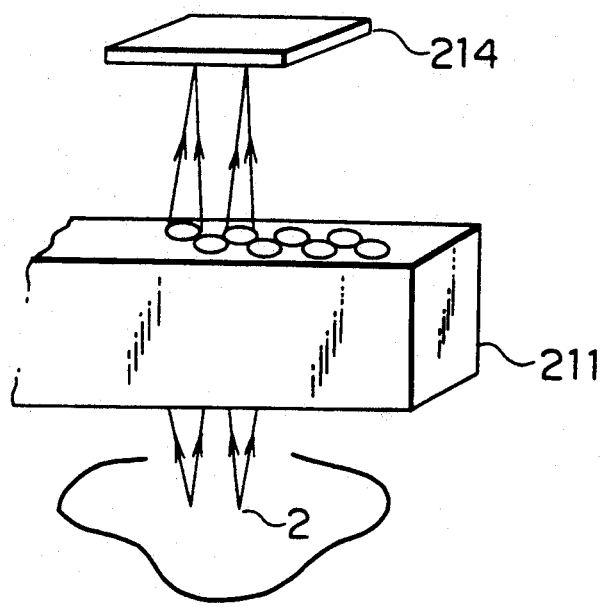
FIG. 27 shows an example of an imaging lens.

The imaging lens 211 of the detecting optical system may be an ordinary lens as shown in FIG. 26 or a refractive index changeable type lens array such as shown in FIG. 27. In either case, if an optical system capable of illuminating the plane waves shown in FIGS. 24 and 25 is used as the illumination optical system 110, there is no structural difference such as in the spatial filter 212, and so forth.

Figure 28:
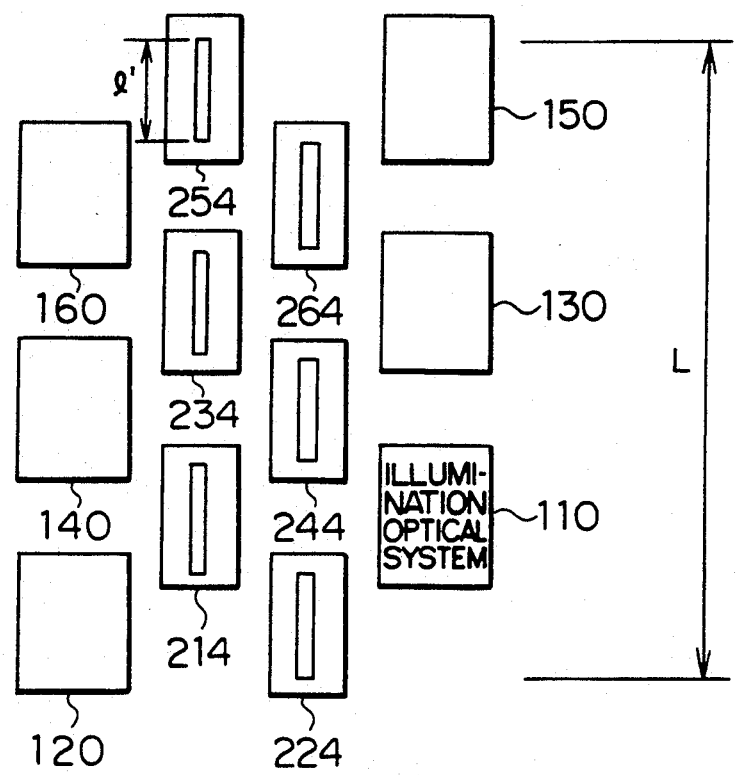
FIG. 28 is a plan view of an embodiment.

FIG. 28 is a plan view of the illumination optical system and the detecting optical system. A plurality of detecting optical systems 210 to 260 and unidimensional detectors 214 to 264 are so arranged as to cover the full zone of the diameter L of the wafer. Each illumination optical system 110-160 is so arranged as to illuminate the detection area of each unidimensional detector 214-264. According to this arrangement, the entire zone of the wafer can be illuminated by the parallel luminous flux, or in other words, by the plane waves.

In the stage system 300, after the wafer 1 is set to the transfer means 301, the wafer transfer means 301 moves in the x direction. Here, the wafer transfer means 301 functions as transfer means for other processing apparatus or in other words, as the transfer system of the film formation unit, the etching unit, the exposure unit, and so forth. Needles to say, the foreign particle inspection apparatus of the present invention may be furnished with this transfer means. The automatic focusing-detection system 312 measures the distance between the wafer and the apparatus of the present invention and the automatic focusing control system 313 controls on the basis of this result so that the distance between the wafer 1 and the apparatus of the present invention becomes optimal. This control may be sufficiently carried out once before the start of the inspection but depending on the level of accuracy of the wafer transfer means 301, the control must be made on the real time basis during the inspection in some cases.

In the signal processing system 410, the detection signal from the unidimensional detector 214 is subjected to A/D conversion by the A/D convertor 411, and passes through the threshold value circuit 412. A binarized one-bit signal is sent to a 5×5 two-dimensional image segmentation circuit 413, and the pattern and the foreign particle are discriminated by a pattern foreign particle judgement circuit 414 in accordance with the logical formula shown in the accompanying drawing. In other words, assuming that the logic value of the point at the center is P(0, 0), a signal of p(0, 0) is judged as a foreign particle when the following formula (1) of the drawing is established and is judged as a pattern when the following formula (2) of the drawing is established.

$$P(0, 0) * \pi P(i, j) = 1 \qquad \text{(FORMULA 1)}$$
$$|i| = 2$$
$$|j| = 2$$
(WHERE * AND $\pi$ ARE LOGICAL PRODUCTS)

$$P(0, 0) * \Sigma P(i, j) = 1 \qquad \text{(FORMULA 2)}$$
$$|i| = 2$$
$$|j| = 2$$
(WHERE $\Sigma$ IS A LOGICAL SUM)

The result of judgement is stored in a pattern memory 415 and the foreign particle memory 416 by the coordinates signals obtained from the fundamental clock of the unidimensional detector 214. A plurality of systems such as three systems are provided for the circuit extending from the threshold circuit 412 to the foreign particle memory 416 and the threshold value of the threshold value circuit 412 is changed step-wise. This circuit construction provides the effect that the circuit scale can be reduced while keeping necessarily sufficient functions.

The signal processing systems 410 to 460 are provided in order to process the signals of the detecting optical systems 210 to 260.

In the data processing system 501, the data from the foreign particle memory 416 are Fourier transformed to foreign particle map data by the FFT circuit 511 and the repetition portion elimination circuit 512 eliminates the repetition portions between the chips. The coordinates and threshold value of the foreign particle data obtained in this manner are stored in the foreign particle memory 513 and when the number of foreign particles is greater than an allowable range, an alarm signal is outputted by the alarm 517. When this alarm signal is outputted, an operation stops the operation of the production line, investigates the cause of the generation of the foreign particles and takes appropriate countermeasures. The map data and coordinates data of the foreign particles are outputted to the display system 516 by the instruction of the microcomputer 515. In the present invention, the pattern data are stored in the memory, too. This data means that the foreign particle inspection is not executed in the pattern portion. Therefore, the ratio of the pattern data to the total area represents the inspection area ratio. If this inspection area ratio is smaller than a predetermined value, there is the possibility of the error of the inspection apparatus or the error of the wafer process. In this case, too, the alarm 517 raises the alarm.

Hereinafter, the operation will be explained with reference to FIGS. 23 to 32.

The present invention pays a specific attention to repetitivity of the patterns in order to inspect foreign particles on very large scale LSIs having miniature patterns formed thereon by a compact inspection apparatus at a high inspection rate and with a high level of accuracy. A large-scale high performance inspection apparatus has been employed conventionally to inspect the full area of a wafer at a high rate and high accuracy. It has been found, however, that it is better to conduct full wafer inspection by sacrificing the full area inspection rather than to conduct the foreign particle inspection on the full area, to improve the yield of the semiconductor fabrication. So long as the conventional apparatus is used, it is essentially necessary to conduct the inspection by sampling the wafers at a suitable frequency, and this method involves the possibility that once any defects occur, large quantities of defects are created unavoidably. However, when the full wafer inspection is carried out, defects such as generation of foreign particles in the equipments and in the process can be detected without effecting the full area inspection of the wafers.

It is therefore noteworthy that the repetition pattern exists with a large ratio in LSIs as typified by memories. This ratio is at least 80% in DRAMs, SPAMs, etc., and is in most cases at least 30% in microcomputers, custom LSIs, and so forth. If the ratio remains at such a level, the inspection of only this repetition portions will be sufficient. Stress detection technique of non-repetition portions using an optical filter is effective in the inspection of the defects and foreign particles of the repetition portions, and the present invention therefore uses this technique. The preparation method of the spatial filter is very important in this method.

Figure 23:
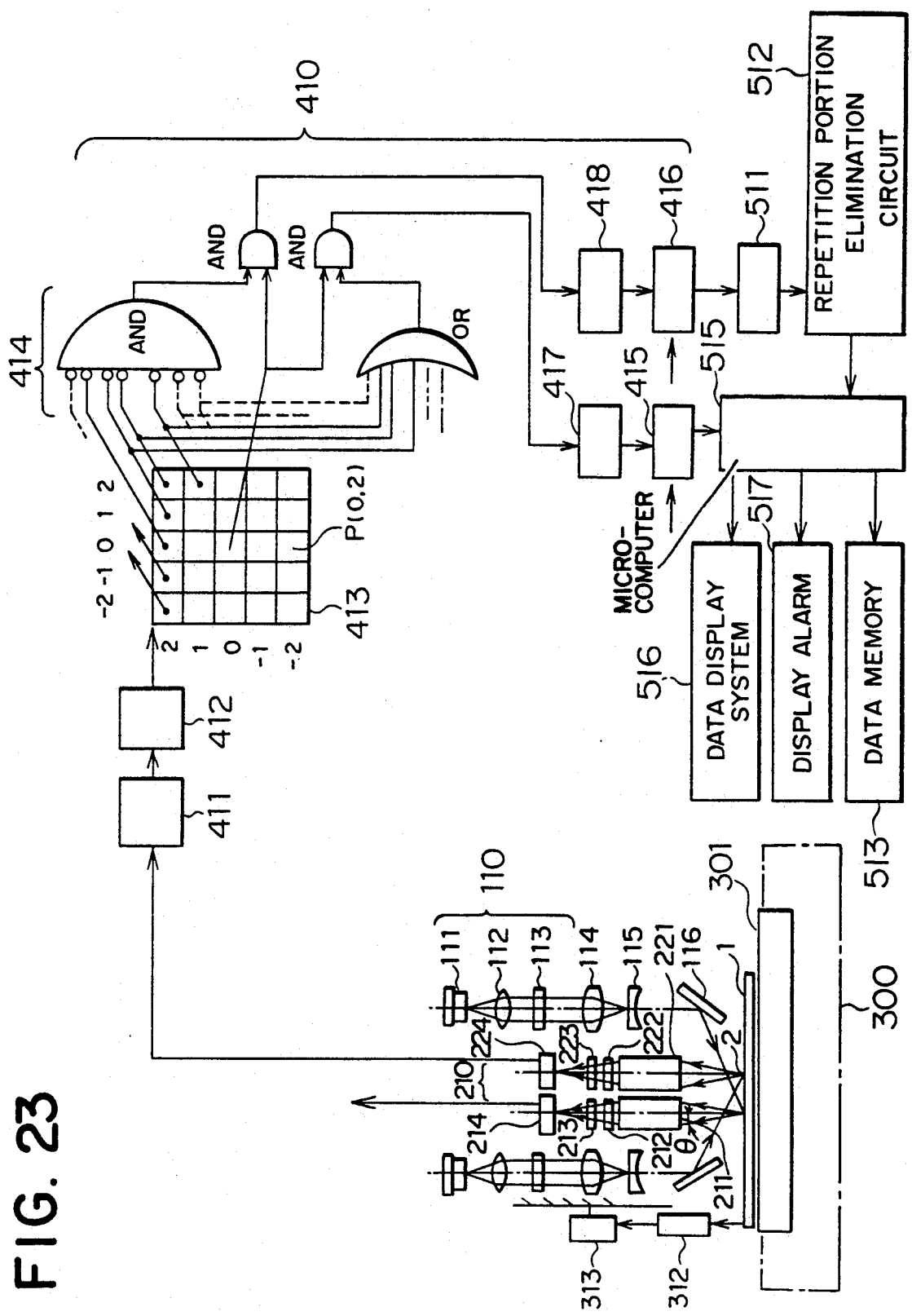
FIG. 23 is a block diagram of a foreign particle inspection apparatus of an embodiment of the present invention.
Figure 29:
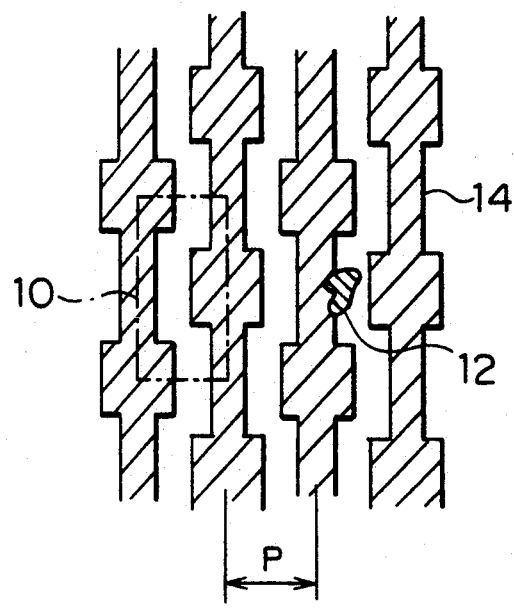
FIG. 29 is a plan view of a pattern of a wafer.
Figure 30:
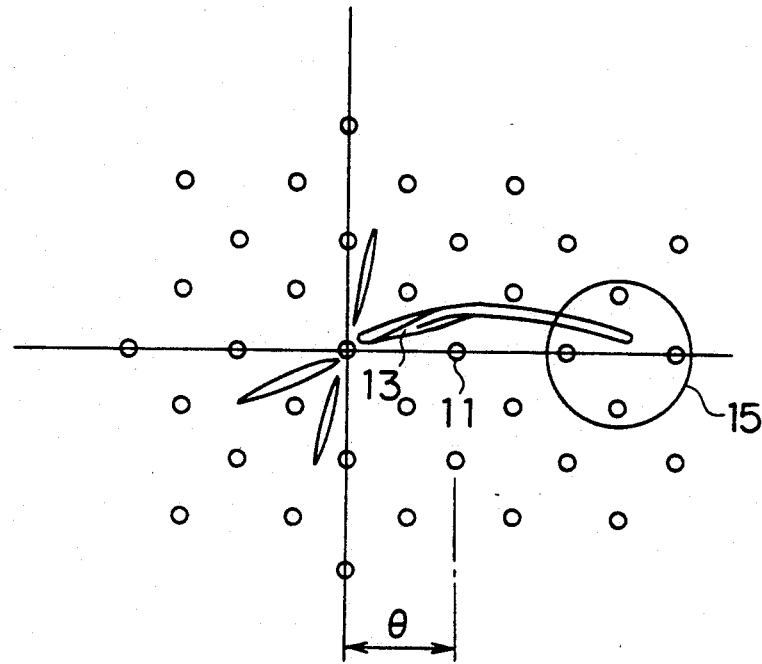
FIG. 30 is a plan view of a diffraction pattern.
Figure 33:
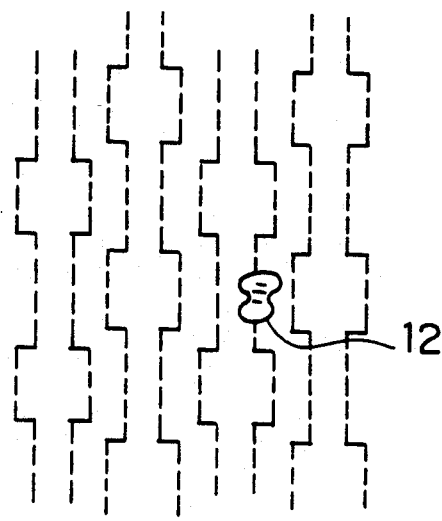
FIG. 33 shows a detection example of foreign particles.

When the light is illuminated on the repetition patterns of the basic pattern 10 shown in FIG. 29 by the apparatus shown in FIG. 23, regular diffraction patterns 11 shown in FIG. 30 can be observed through the spatial filter 212. This diffraction pattern 11 results from diffraction of the pattern shown in FIG. 29. If any foreign particle 12 exists on FIG. 29, the diffraction light from the foreign particle becomes irregular shapes different from the regular diffraction pattern 11 and are observed as a pattern 13 in FIG. 30, for example. Therefore, if a filter which blocks the diffraction pattern 11 is disposed on the spatial filter 212, data on the pattern 14 are deleted and only the data of the foreign particle 12 are observed on the unidimensional detector 214 as shown in FIG. 33. In other words, the present invention detects selectively only the foreign particle 12.

Here, the pitch p of the patterns 14 and the pitch $\theta$ of the diffraction pattern 11 (expressed by the angle of the diffraction pattern incident into the imaging lens 211 from the observation point 2) are represented by the following relational formula (3) as the wavelength $\lambda$ of the beam of light emitted from the illumination optical system 110:

$$sin\theta = \theta/p \qquad \ldots (3)$$

Accordingly, the smaller the value p, the greater becomes the value $\theta$. In other words, the more the LSI is miniaturized and the smaller the value p, the greater the value $\theta$ of the diffraction pattern. In consequence, there can be obtained the advantage that the diffraction pattern incident into the imaging lens 211 decreases and the shape of the spatial filter can be more simplified. In the case of the same product, the position pitch of the basic pattern 10 remains unaltered even though the shape of the basic pattern 10 changes. This means that the basic shape of the diffraction pattern remains unchanged. In other words, so long at the same product is inspected, the shape of the diffraction pattern does not substantially change and hence, the shape of the spatial filter for blocking the light does not substantially change, either. On the basis of this characterizing feature, the present invention pays a specific attention to the fact that even when the shape of the diffraction pattern for each fabrication step is measured for each product and then a spatial filter for blocking all their diffraction patterns is prepared, the spatial filter does not completely block the light to the aperture of the imaging lens. If such a filter which blocks all the diffraction patterns for each fabrication step is used, the necessity for the exchange of the spatial filters can be eliminated. This arrangement is particularly effective for the fabrication line of memories because the kinds of the products are limited and the change of the products does not much occur.

If a refractive index changeable type lens array is used as the imaging lens 212, the present invention can further reduce the scale of the apparatus. The refractive index changeable type lens array can constitute a compact optical system and for this reason, has been used for facsimiles, electronic copying machines, and so forth. This refractive index changeable type lens array is effective for accomplishing the object of rendering the optical system compact. However, the present invention must use the spatial filter. The refractive index changeable type lens array, too, has a Fourier transform plane but it has not been realized conventionally that the spatial filter can be used for the former. The present invention achieves a compact foreign particle monitor using the refractive index changeable type lens array on the basis of this concept that the spatial filter can be used for the refractive index changeable type lens array.

Figure 31:
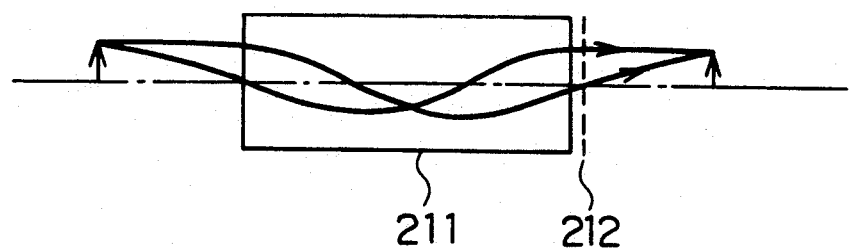
FIG. 31 is a refractive index changeable lens.

The structure and operation of the spatial filter are the same as those already described, and one spatial filter may be so disposed as to correspond to each lens of the lens array. The position of each spatial filter of this refractive index changeable type lens array exists on the end surface of the lens on its outgoing side as shown in FIG. 31.

Figure 32A:
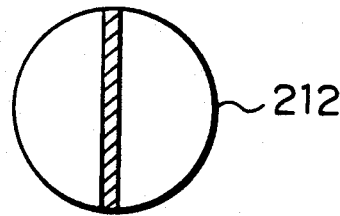
FIGS. 32(a) to 32(c) are plan views of a spatial filter.
Figure 32B:
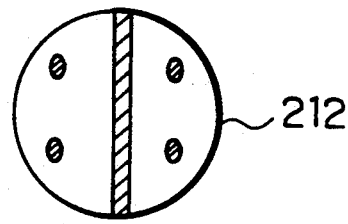
Figure 32C:
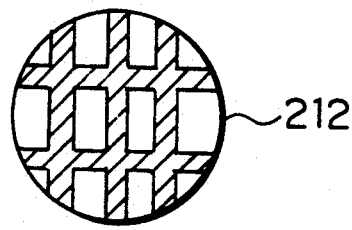

FIG. 32 shows the shapes of the spatial filters. Among them, the filter on the straight line such as shown in FIG. 32(a) can be used most easily and provides the effects for arbitrary patterns. To obtain higher discrimination performance than the filter shown in FIG. 32(a), the filter having the shape such as shown in FIG. 33(b) must be used. Furthermore, FIG. 32(c) shows an example of the shapes which can be used for all the fabrication steps of the product.

When the foreign particle inspection apparatus of the present invention is introduced into the production line, all the wafers passing through the line can be inspected and the increase of the foreign particles can be detected on the real time basis. Accordingly, the occurrence of large quantities of defective products due to the generation of the foreign particles can be in advance prevented and the production yield can be therefore improved.

Having the construction as described above, the present invention can execute the foreign particle inspection in the mass production line of the semiconductor fabrication process on the real time basis, can minimize the defective products and can greatly contribute to the improvement in the yield of the product.

We claim:

1. A method of inspecting foreign particles on a product substrate in a mass production line of a semiconductor fabrication process, comprising the steps of:
   transferring the product substrate along a path of transferring means provided at at least one predetermined position in the mass production line of the semiconductor fabrication process;
   detecting a rotation direction of repetitive patterns of a circuit pattern being formed on the transferred product substrate;
   illuminating light of a substantially slit shape on the surface of the product substrate transferred along the path of the transferring means;
   detecting with a detecting means information of a surface of the product substrate including detecting scattered light from foreign particles existing on the surface of the product substrate transferred along the path of the transferring means and illuminated by the light of substantially slit shape through a detecting lens;
   aligning relatively the detected direction of the repetitive patterns of the product substrate and a direction of the detecting means; and
   determining a state of foreign particles on the product substrate transferred along the path of the transferring means in accordance with the detection of the scattered light.

2. A method according to claim 1, wherein the detecting means includes a spatial filter provided on a Fourier transform plane of the surface of the product substrate, and the step of aligning includes aligning relatively the detected direction of the respective patterns of the product substrate and a direction of the spatial filter, the spatial filter enabling shielding of diffraction light from the repetitive patterns of the circuit pattern image on the Fourier transform plane through the detecting lens.

3. A method according to claim 2, wherein an illumination means serves for illuminating light of the substantially slit shape on the surface of the product substrate and the detecting means includes a photo-detector array detecting the scattered light from the foreign particles and providing an output signal indicative thereof, the step of determining the state of foreign particles includes effecting determination in accordance with the output signal from the photodetector array.

4. A method according to claim 3, wherein the step of detecting the rotation direction of repetitive patterns of the circuit pattern includes detecting a rotation direction of an orientation flat of the product substrate, the product substrate being a product wafer.

5. A method according to claim 4, wherein the step of aligning relatively includes controlling the rotation of the product wafer to effect the relative alignment.

6. A method according to claim 3, wherein the step of illuminating includes illuminating light of substantially slit shape in a zig zag arrangement so as to effect overlapping of adjacent illumination without interference with the detecting lens.

7. A method according to claim 3, wherein the detecting lens is a detecting lens array and a length of the detecting lens array and a length of the substantially slit shape light corresponds substantially to a diameter of the product wafer so as to enable detection of foreign particles on the product wafer during transfer along the path of the transferring means.

8. A method according to claim 3, wherein the step of determining the state of foreign particles on the product wafer includes effecting display on a monitor.

9. A method according to claim 3, wherein the step of detecting the state of foreign particles on the product wafer includes effecting calibration in accordance with a measured refractive index of the product wafer.

10. A method according to claim 3, wherein the detecting lens for enabling detection of the scattered light has a focal depth of 0.1 to 0.5 mm.

11. A method according to claim 6, wherein the step of illuminating in a zig zag pattern includes effecting illumination from opposite sides.

12. A method according to claim 1, wherein the step of illuminating includes utilizing white light and illuminating the surface of the product substrate at an oblique angle with respect to a perpendicular direction thereto.

13. A method according to claim 1, further comprising the step of determining characteristics of a production apparatus of the mass production line based upon the detected rotational direction of the product substrate and the determined state of foreign particles with respect to the detected rotational position.

14. A method according to claim 1, wherein the step of illuminating includes illuminating the surface of the product wafer at an oblique angle with respect to a perpendicular direction thereof.

15. A method according to claim 1, wherein the step of determining includes determining a distribution of foreign particles in accordance with the detection of the scattered light and a two-dimensional coordinate determined for the product substrate based upon the detected rotation direction.

16. A method according to claim 3, wherein the step of illuminating includes utilizing coherent light.

17. A method according to claim 3, further comprising the step of enabling change of a filtering pattern of the spatial filter.

18. A method according to claim 1, further comprising the steps of for mass production start-up of the semiconductor fabrication process, supplying at least one sampling wafer as the product substrate to at least one gas supplier means and a plurality of production apparatus of the mass production line so as to process the supplied at least one sampling wafer in accordance therewith, and determining a generation of a foreign substance and a contaminent.

19. An apparatus for inspecting foreign particles on a product substrate in a mass production line in a semiconductor fabrication process, comprising:

transferring means provided at least one predetermined position in the mass production line of the semiconductor fabrication process for transferring the product substrate along a path thereof;

means for detecting a rotation direction of repetitive patterns of a circuit pattern being formed on the transferred product substrate;

illuminating substantially slit shape light on the surface of a product substrate transferred along the path of the transferring means;

detecting means for detecting information of a surface of the product substrate through a detecting lens including detecting scattered light from foreign particles existing on the surface of the product substrate transferred along the path of the transferring means and illuminated by the substantially slit shape light through the detecting lens;

means for enabling relative alignment of the detected direction of the repetitive patterns of the product substrate and a direction of the detecting means; and means for determining a state of foreign particles on the product substrate transferred along the path of the transferring means in accordance with the detection of the scattered light.

20. Apparatus according to claim 19, wherein the detecting means includes a spatial filter provided on a Fourier transform plane of the surface of the product substrate, and the means for enabling alignment includes means for relatively aligning the detected direction of the respective patterns of the product substrate and a direction of the spatial filter, the spatial filter enabling shielding of diffraction light from the repetitive patterns of the circuit pattern imaged on the Fourier transform plane through the detecting lens, the determining means includes determining a distribution of foreign particles in accordance with an output of the detection means and in accordance with the means for enabling alignment.

* * * * *